US012299624B2

(12) United States Patent
Lowry et al.

(10) Patent No.: US 12,299,624 B2
(45) Date of Patent: May 13, 2025

(54) ARTIFICIAL INTELLIGENCE TRAINING FOR MEDICAL STAFF

(71) Applicants: Candice E. Lowry, Colorado Springs, CO (US); Benjamin J. Kwitek, Canon City, CO (US)

(72) Inventors: Candice E. Lowry, Colorado Springs, CO (US); Benjamin J. Kwitek, Canon City, CO (US)

( * ) Notice: Subject to any disclaimer, the term of this patent is extended or adjusted under 35 U.S.C. 154(b) by 0 days.

(21) Appl. No.: 18/363,198

(22) Filed: Aug. 1, 2023

(65) Prior Publication Data

US 2023/0377083 A1 Nov. 23, 2023

Related U.S. Application Data

(63) Continuation of application No. 17/938,260, filed on Oct. 5, 2022, now Pat. No. 11,842,418, which is a
(Continued)

(51) Int. Cl.
  *G06Q 50/28* (2012.01)
  *G01G 19/52* (2006.01)
  (Continued)

(52) U.S. Cl.
  CPC .............. *G06Q 10/08* (2013.01); *G01G 19/52* (2013.01); *G01P 13/00* (2013.01); *G01V 8/10* (2013.01);
  (Continued)

(58) Field of Classification Search
  CPC ........ G06Q 10/08; G06Q 20/14; G06Q 40/08; G16H 40/20; G06F 18/25; G01G 19/52;
  (Continued)

(56) References Cited

U.S. PATENT DOCUMENTS 7,962,544 B2 * 6/2011 Torok ..................... H04L 67/12
                                                              709/200
8,346,632 B2   1/2013 Saghbini
(Continued)

FOREIGN PATENT DOCUMENTS

DE    202006010036 U1    8/2006
EP       1246097 A1 * 10/2002 ............. G06Q 10/06
WO    2011035329 A2    3/2011

OTHER PUBLICATIONS

Omnicell, XT Automated Dispensing Cabinets and Drawers Brochure. XT Cabinet Specifications. Copyright 2020.
(Continued)

*Primary Examiner* — Chico A Foxx
(74) *Attorney, Agent, or Firm* — Welsh Flaxman & Gitler LLC

(57) ABSTRACT

An inventory tracking and management system includes storage devices comprising carts, cabinets, or shelves, sensors and/or monitoring devices associated with the storage devices, a central database connecting the storage devices, sensors, and monitoring devices within a hospital, and a processing server associated with the central database. The processing server including a software system controlling operation of the inventory tracking and management system.

15 Claims, 20 Drawing Sheets

Related U.S. Application Data continuation of application No. 16/885,920, filed on May 28, 2020, now Pat. No. 11,495,348.

(60) Provisional application No. 62/853,236, filed on May 28, 2019.

(51) Int. Cl.
| | |
|---|---|
| *G01P 13/00* | (2006.01) |
| *G01V 8/10* | (2006.01) |
| *G06F 18/25* | (2023.01) |
| *G06Q 10/08* | (2023.01) |
| *G06Q 20/14* | (2012.01) |
| *G06Q 40/08* | (2012.01) |
| *G07C 9/00* | (2020.01) |
| *G08B 7/06* | (2006.01) |
| *G16H 40/20* | (2018.01) |
| *G06N 20/00* | (2019.01) |
| *G06V 20/52* | (2022.01) |

(52) U.S. Cl.
CPC .............. *G06F 18/25* (2023.01); *G06Q 20/14* (2013.01); *G06Q 40/08* (2013.01); *G07C 9/00563* (2013.01); *G07C 9/0069* (2013.01); *G07C 9/00896* (2013.01); *G08B 7/06* (2013.01); *G16H 40/20* (2018.01); *G06N 20/00* (2019.01); *G06V 20/52* (2022.01); *G07C 2009/0092* (2013.01)

(58) Field of Classification Search
CPC ....... G01P 13/00; G01V 8/10; G07C 9/00563; G07C 9/0069; G07C 9/00896; G07C 2009/0092; G08B 7/06; G06N 20/00; G06V 20/52
See application file for complete search history.

(56) References Cited

U.S. PATENT DOCUMENTS

| | | | |
|---|---|---|---|
| 11,087,273 B1 | 8/2021 | Bergamo | |
| 2005/0096962 A1* | 5/2005 | Narasimhan ... | G06Q 10/063116 705/7.21 |
| 2007/0290030 A1 | 12/2007 | Fox et al. | |
| 2009/0008443 A1* | 1/2009 | Levovitz ................ | G16H 10/65 235/487 |
| 2010/0036755 A1 | 2/2010 | Saghbini | |
| 2011/0140381 A1 | 6/2011 | Rossini | |
| 2013/0253952 A1 | 9/2013 | Burke et al. | |
| 2013/0282392 A1 | 10/2013 | Wurm | |
| 2013/0320820 A1 | 12/2013 | Rahilly | |
| 2015/0205923 A1 | 7/2015 | Sobie | |
| 2015/0223890 A1 | 8/2015 | Miller et al. | |
| 2015/0332209 A1 | 11/2015 | DeBusk et al. | |
| 2015/0366377 A1 | 12/2015 | Savage et al. | |
| 2016/0307150 A1 | 10/2016 | Rogers et al. | |
| 2017/0262797 A1 | 9/2017 | Wicks et al. | |
| 2018/0121869 A1 | 5/2018 | Bradley et al. | |
| 2018/0121873 A1* | 5/2018 | Walsh ................ | G06Q 10/0836 |
| 2018/0150613 A1 | 5/2018 | Bossi et al. | |
| 2018/0232577 A1 | 8/2018 | Lipsey et al. | |
| 2019/0051407 A1 | 2/2019 | Van Der Veer et al. | |
| 2020/0118154 A1 | 4/2020 | Schumacher et al. | |
| 2020/0121556 A1* | 4/2020 | Tian ...................... | A61H 39/02 |
| 2020/0160053 A1 | 5/2020 | Lipsey et al. | |
| 2020/0258094 A1 | 8/2020 | Abrams | |
| 2020/0273581 A1* | 8/2020 | Wolf ...................... | G16H 40/63 |
| 2020/0317445 A1 | 10/2020 | Schultz et al. | |
| 2020/0335208 A1* | 10/2020 | Talmor ................... | G16H 40/60 |
| 2020/0364660 A1 | 11/2020 | Hines et al. | |
| 2020/0410434 A1 | 12/2020 | Fly et al. | |
| 2020/0410446 A1 | 12/2020 | Rahilly et al. | |
| 2021/0133670 A1 | 5/2021 | Cella et al. | |
| 2021/0150159 A1 | 5/2021 | Volkerink et al. | |
| 2021/0157998 A1* | 5/2021 | Rodriguez ............. | G06V 20/20 |
| 2021/0182996 A1 | 6/2021 | Cella et al. | |
| 2022/0318739 A1 | 10/2022 | Bradley et al. | |
| 2022/0358478 A1 | 11/2022 | Mohuddin et al. | |
| 2023/0252426 A1* | 8/2023 | Fogg .............. | G06Q 10/063116 705/7.21 |

OTHER PUBLICATIONS

Becton, Dickinson and Company. BD Pyxis™ ES platform solutions specifications. Copyright 2019.

Becton, Dickinson and Company. Pyxis® ES platform solutions for hospitals and IDNs. Pyxis MedStation® ES system. Copyright 2012. www.carefusion.com.

Becton, Dickinson and Company. BD Pyxis™ Cubie™ Pockets. Copyright 2018.

Becton, Dickinson and Company. Committing to the journey toward zero errors and zero waste. BD Connected Medication Management. Copyright 2019.

* cited by examiner

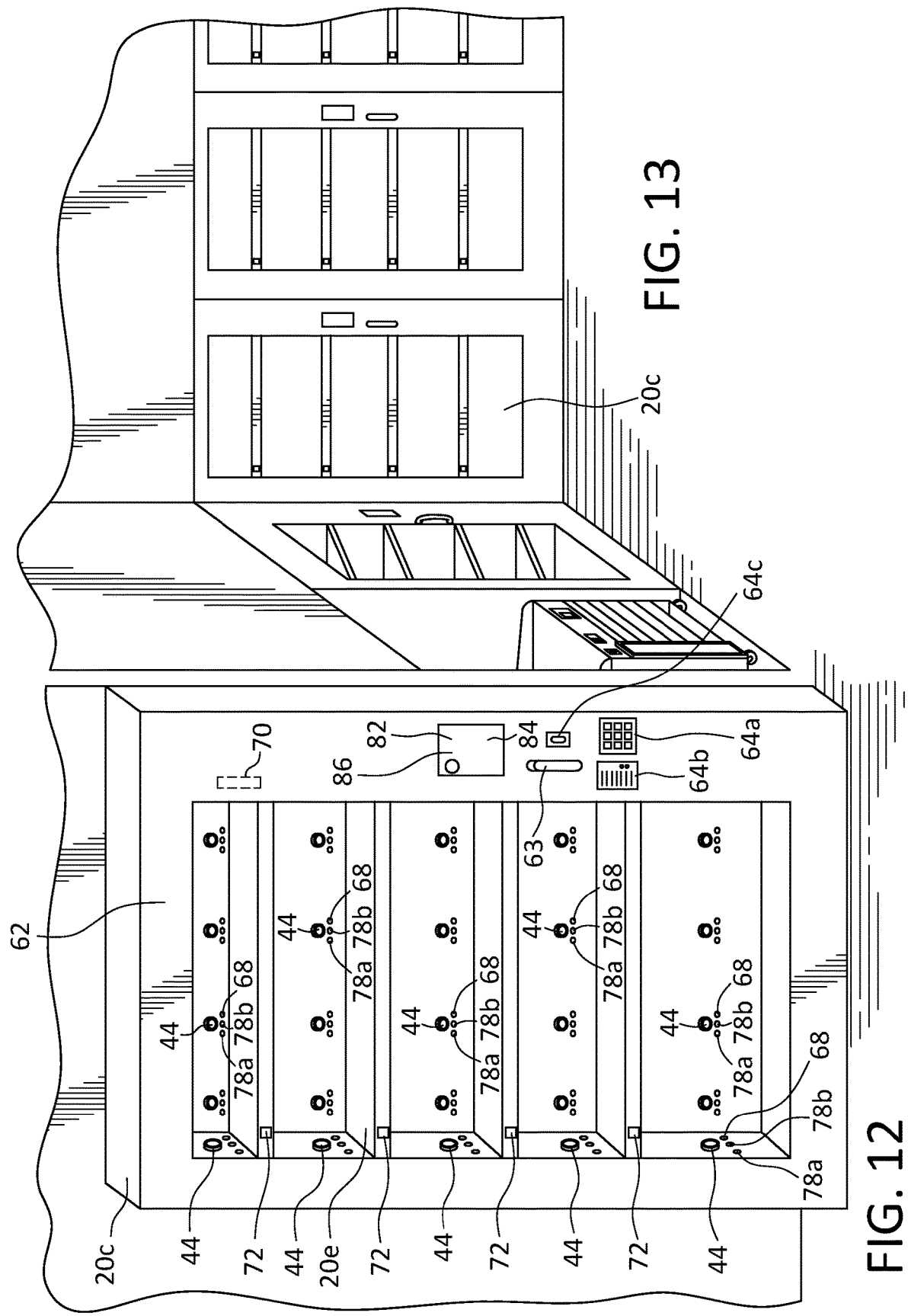

Emergency Department Trauma Center Inventory List

| CATEGORIES | ITEMS | VARIOUS TYPES | AGE | VARIES SIZES |
|---|---|---|---|---|
| | 1mL syringe | | | |
| | 3mL syringe | | | |
| | 5mL syringe | | | |
| | 10mL syringe | | | |
| | 2omL syringe | | | |
| | alcohol pads | | | |
| | puncture needles (vial needles) | | | |
| | IV tubing cap, syringe cap | | | |
| | bandaids | * | | * |
| | transpore tape | | | * |
| | silk tape | | | * |
| | mouth swabs | | | |
| | ChloraPrep swabs | | | |
| | hemaoccult test | | | |
| | tongue depressor | | | |
| | gauze pads 2x2 | | | |
| | gauze pads 4x4 | | | |
| | gloves | * | | * |
| | temporal thermometer, covers | | | |
| | tympanic thermometer, covers | | | |
| | oral thermometer, covers | | | |
| | blood pressure cuffs | | * | * |
| | 500mL NS IV Fluid | | | |
| | 1000mL NS IV Fluid | | | |
| | IV pump tubing | | | |
| | IV gravity tubing | | | |
| | IV pumps | | | |
| | ECG electrodes | | | |
| | multi-parameter patient monitor | | | |
| | suction canister | | | |
| | suction tubing | | | |
| | yankauer | | | |

FIG. 16A

| Item | Col 1 | Col 2 | Col 3 |
|---|---|---|---|
| pads, chuck, briefs | * |  | * |
| urinals |  |  |  |
| bedpans | * |  |  |
| urine sample cups |  |  |  |
| lubricants |  |  |  |
| indwelling foley catheter |  |  |  |
| male urinary straight catheter |  |  |  |
| female urinary straight catheter |  |  |  |
| barrier wipes |  |  |  |
| pulse oximetry |  | * | * |
| coban |  |  | * |
| IV start kits |  | * |  |
| tourniquet |  |  |  |
| butterfly needle |  |  |  |
| 18 gauge needle |  |  |  |
| 20 gauge needle |  |  |  |
| 22 gauge needle |  |  |  |
| 24 gauge needle |  |  |  |
| Normal Salineflush syringes |  |  |  |
| nasal cannulas |  | * | * |
| simple mask |  | * | * |
| non-rebreather mask |  | * | * |
| emesis bags |  |  |  |
| kLeenex |  |  |  |
| IV extension |  |  |  |
| Vacutainers - blood collection vials | * |  |  |
| ED stretcher |  |  |  |
| washcloths |  |  |  |
| towels |  |  |  |
| drapes |  |  |  |
| sheets |  |  |  |
| patient gowns |  | * | * |
| pillows |  |  |  |
| pillowcases |  |  |  |
| medication cups |  |  |  |

FIG. 16B

| | | | |
|---|---|---|---|
| intramuscular needles | | * | |
| sterile gLoves | | * | |
| glucose monitor kit | | | |
| flu swabs | | | |
| throat swabs | | | |
| wheelchairs | | | |
| rectal thermometer, covers | | | |
| blood culture vials | | * | |
| implanted port access supplies | | | |
| sterile procedure kits | * | | |
| sterile supplies | * | | |
| NG tube supplies | * | * | * |
| pediatric supplies | * | * | * |
| urinary supplies | * | * | * |
| hygiene supplies | * | | * |
| disposable stethoscopes | | | |
| batteries | * | | |
| face masks | * | | |
| eye protection | | | |
| ear plugs | | | |
| safety pins | | | |
| seizure pads | | | |
| linen carts | | | |
| soft restraints | | | |
| hard restraints | | | |
| respiratory supplies | * | * | * |
| enema supplies | * | | |
| oral contrast supplies | | | |
| filters | * | | |
| secondary IV tubing | | | |

FIG. 16C

Emergency Department Trauma Center Inventory List

| CATEGORIES | ITEMS | WEIGHT BASE | AGE | VARIES SIZES |
|---|---|---|---|---|
| MACHINES | 12-Lead ECG Machine | | | |
| | ventilators | * | | |
| | portable ultrasound | | | |
| | portable x-ray | | | |
| | computers at desks | | | |
| | computers on wheels | | | |
| | computers in rooms | | | |
| | CPAP -continuous positive airway pressure | | * | |
| | BiPAP -bilevel positive airway pressure | | * | |
| | continuous capnography monitor | | | |
| | portable pulse oximetry device | | | |
| | blanket warmers | | | |
| | IV pumps | | | |
| | autoclave | | | |
| | GlideScope | | | |
| | babywarmer, incubator, isolette | | | |
| | defibrillator/pacer monitor | | | |
| | Pulsara iPads | | | |
| | language assistive device | | | |
| | telemonitor | | | |
| | slit lamp | | | |
| | head lamp | | | |
| | vital signs machines | | | |
| | FAST ultrasound machine | | | |
| | multi-parameter patient monitor | | | |
| | Level 1 massive transfusion machine | | | |
| | cauterize pen | | | |
| | adult weight scale | | | |
| | infant weight scale | | | |
| | dictation devices | | | |
| | CT scans | * | | |
| | Toco monitor | | | |
| | bladder scanner | | | |
| | hair hugger | | | |
| | fetal heart monitor | | | |
| | pacemaker analyzer | | | |
| | pyxis machines | | | |
| | IV fluid warmer | | | |

FIG. 16D

Emergency Department Trauma Center Inventory List

| CATEGORIES | ITEMS | VARIOUS TYPES | AGE | VARIES SIZES |
|---|---|---|---|---|
| WOUND CARE | gauze pads | | | * |
| | mepilex | | | * |
| | gauze rolls | | | * |
| | ABA pads | | | * |
| | bandaids | | | * |
| | tegaderm | | | * |
| | QuickClot | | | * |
| | tourniquets | | | |
| | sterile water bottles | | | * |
| | irrigation shields | * | | * |
| | NS bottles | | | * |
| | tube gauze | | | * |
| | betadine | | | * |
| | hibiclens | | | * |
| | coban | | | * |
| | kerlix | | | * |
| | xeroform | * | | * |
| | chlorhexidine | | | * |
| | vaseline gauze | | | * |
| | paper tape | | | * |
| | transpore polyethylene tape | | | * |
| | foam tape | | | * |
| | butterfly stitches | | | * |
| | neosporin | | | * |
| | lodoform packing | * | | * |
| | disposable measuring tape | | | * |
| | disposable marker | | | * |
| | culture collection kits | * | | * |
| | surgical scrub brush | | | * |
| | soap basin | | | * |
| | ace wraps | | | * |
| Ortho Supplies | splints | * | | * |
| | c-collars | * | | * |
| | arm slings | * | * | * |
| | coban | | | * |
| | ace-wraps | | | * |
| | reusable ice pack | | | |
| | snap ice pack | | | |
| | crutches | | | * |
| | immobilizers | * | | * |
| | ortho shoe | | | * |
| | air-splint | | | * |
| | hover mat | | | * |
| | boots | | | * |

FIG. 16E

Emergency Department Trauma Center Inventory List

| CATEGORIES | ITEMS | VARIOUS TYPES | AGE | VARIES SIZES |
|---|---|---|---|---|
| OB/GYN CART | speculum | | | |
| | speculum light | | | |
| | disposable light cover | | | |
| | maternity pads | | | |
| | mesh underwear | | | |
| | chucks | | | |
| | OB/GYN swabs | | | |
| | STD swabs | | | |
| | wet prep | | | |
| | adjustable foot rests | | | |
| | lubricant | | | |
| | ring forceps | | | * |
| | forceps | * | | |
| SUTURE CART | dressings | * | | * |
| | lidocaine vial | * | | |
| | lidocaine w/epi vial | | | |
| | sterile water vial | | | |
| | needles | * | | * |
| | IM needles | | | * |
| | sterile water bottles | | | |
| | NS water bottles | | | |
| | sterile gloves | | | * |
| | sutures | | | |
| | needle w/suture kits | * | | * |
| | lancet kits, abcess kits | | | |
| | suture kits | * | | * |
| | chlorhexidine swabsticks | | | |
| | betadine | | | |
| | dermabond | | | |
| | QuickClot | | | * |
| | suture/staple removal kit | | | |
| | staple gun | | | |
| EENT CART | Morgan Lens irrigation | | | |
| | otoscope, covers | | | |
| | opthamloscope, covers | | | |
| | litmus paper | | | |
| | tongue depressor | | | |
| | nose clamps | | | |
| | rhino rockets | | | |
| | packing | * | | |
| | forceps | * | | * |
| | dressings | * | | * |
| | eye pad | | | |
| | eye shieLd | | | |
| | cauterize pen | | | |
| | pen light | | | |
| | tono pen | | | |
| | ear care supplies | * | | |
| | eye care supplies | * | | |
| | nosebleed supplies | * | | |

FIG. 16F

| Category | Item | | | |
|---|---|---|---|---|
| | throat supplies | * | | |
| PEDIATRIC CART | monitoring items | * | * | * |
| | vital signs items | * | * | * |
| | respiratory diapers | | | * |
| | diapers | | | * |
| | pedialyte | | | |
| | IV start kits | | | * |
| | needles | | | * |
| | tourniquets | | * | |
| | bottles | | | |
| | nipples | | | |
| | sippy cups | | | |
| | feeding tubes | | | * |
| | airway supplies | * | * | * |
| | arm board | | | * |
| | intranasal mucosal atomization | | | |
| | measuring tape, urinary supplies | | | |
| NEONATE CART | bulb syringe | | | |
| | measuring tape | | | |
| | hats | | | |
| | socks | | | |
| | temperature probe | | | |
| | thermometers | | | |
| | feeding tubes | * | * | * |
| | lancets | | | |
| | IV start kits | | | * |
| | needles | | | * |
| | delivery kit | | | |
| | umbilical cord clamps | | | |
| | monitoring items | * | * | * |
| | vital signs items | * | * | * |
| | airway supplies | * | * | * |
| | respiratory supplies | * | * | * |
| | cord blood sample kit | | | |
| | arm board | | | |
| | urinary supplies | | | * |
| ORTHO CART | measuring tape | | | |
| | ortho-Glass fiberglass | | | |
| | Fluff-E | | | * |
| | coban | | | * |
| | ace-wrap | | | * |
| | tube gauze | | | |
| | finger supplies | * | | * |
| | tourniquet | | | |
| | dressings | * | * | * |
| KITS | Rapid Sequence Intubation Kit (RSI) | | | |
| | tPA kit | | | |
| | epistaxis kit | | | |
| | eye kit | | | |
| | delivery kit | | | |

FIG. 16G

Emergency Department Trauma Center Inventory List

| CATEGORIES | ITEMS | VARIOUS TYPES | AGE | VARIES SIZES |
|---|---|---|---|---|
| TRAUMA/CODE CRASH CARTS | defibrillator/ pacer machine | | | |
| | pediatric defib pads | | * | |
| | adult defib pads | | | |
| | ECG electrodes | | * | |
| | manual blood pressure cuff | | | * |
| | alcohol swabs | | | |
| | amiodarone | | | |
| | atropine | | | |
| | sodium bicarbonate | | | |
| | calcium chloride | | | |
| | sodium chloride | | | |
| | dextrose | | | |
| | dopamine | | | |
| | epinephrine | | | |
| | sterile water | | | |
| | lidocaine | | | |
| | povidine-iodine | | | |
| | vasopressin | | | |
| | salineflushes | | | |
| | endotracheal tubes | | | * |
| | nasopharyngeal airways | | | * |
| | oropharyngeal airways | | | * |
| | laryngoscope handle | | | |
| | laryngoscope blades | | | * |
| | flashlight, extra batteries | | | |
| | syringes | * | | * |
| | stylets | | | |
| | bite block | | | |
| | tongue depressors | | | |
| | IV start kits | | | |
| | angiocatheters 14g and 16g | | | * |
| | chloraprep | | | |
| | betad i n e | | | |
| | luer lock syringes | | | |
| | tourniquet | | | |
| | vacutainers | * | | |
| | spinal needles | | | * |
| | needles | * | | * |
| | 3-way stopcock | | | |
| | tape | * | | * |
| | armboards | | | * |
| | ABG syringes | | | |
| | ABG sampling kits | | | |
| | tubing | * | | * |
| | IV solutions | * | | * |
| | sterile gloves | | | * |
| | sutures | * | | * |
| | suction supplies | * | | |
| | salem pump | | | |
| | crichothyroidectomy kit | | | |
| | cut down pack | | * | |
| | drapesfor sterilefield | | | |
| | yankauer | | | |
| | large bore needle with syringe | | | |
| | lumbar puncture kit | | | |

FIG. 16H

Emergency Department Trauma Center Inventory List

| CATEGORIES | ITEMS | VARIOUS TYPES | AGE | VARIES SIZES |
|---|---|---|---|---|
| TRAUMA/CODE | ambu bags | | * | * |
| | gloves | | | * |
| | needles | * | | * |
| | tubing | * | | |
| | IV fluids | * | | * |
| | multi parameter patient monitor | | | |
| | FAST ultrasound | | | |
| | GlidaScope | | | |
| | difficult airway cart | | | |
| | sterile kits | * | | |
| | surgical caps | | | |
| | face masks | | | |
| | disposable exposure gowns | | | |
| | booties | | | |
| | respiratory supplies | * | * | * |
| | linens | * | | |
| | level 1 massive transfusion machine | | | |
| | chest tube supplies | | | |
| | rib splitters | | | |
| | pelvic binder | | | |
| | backboard | | | |
| | x-ray aprons | | | |
| | dressings, wound supplies | * | | * |
| | arterial line supplies | * | | |
| | Central venous pressure supplies | * | | |
| | surgical supplies | * | | |
| | central line supplies | * | | |
| | IV fluid warmer | | | |
| | pyxis | | | |
| | wound irrigation | * | | |
| | intraosseous access kit | | | |
| | nasogastric tube | | | * |
| | orogastric tube | | | * |
| | blood tubing | | | |
| | c-collars | * | | * |
| | hip splint | | | |
| | traction | * | | |
| | balloon extractor, retrieval | | | |
| | ablation devices | * | | |
| | tape | * | | * |

FIG. 16I

ARTIFICIAL INTELLIGENCE TRAINING FOR MEDICAL STAFF

CROSS REFERENCE TO RELATED APPLICATION

This application is a continuation of U.S. patent application Ser. No. 17/938,260, entitled "ARTIFICIAL INTELLIGENCE STORAGE AND TRACKING SYSTEM FOR EMERGENCY DEPARTMENTS AND TRAUMA CENTERS", filed Oct. 5, 2022, which is a continuation of U.S. patent application Ser. No. 16/885,920, entitled "ARTIFICIAL INTELLIGENCE STORAGE AND TRACKING SYSTEM FOR EMERGENCY DEPARTMENTS AND TRAUMA CENTERS." filed May 28, 2020, which claims the benefit of U.S. Provisional Patent Application Ser. No. 62/853,236, entitled "ARTIFICIAL INTELLIGENCE STORAGE AND TRACKING SYSTEM FOR EMERGENCY DEPARTMENTS AND TRAUMA CENTERS," filed May 28, 2019, which are incorporated herein by reference.

BACKGROUND OF THE INVENTION

1. Field of the Invention

The present invention relates to an inventory tracking and management system.

2. Description of the Related Art

Hospital Emergency Rooms (ER or ERs) have always been busy and chaotic places. The variables encountered on a daily basis are overwhelming and include: the facility, the day and time, the doctors, the nurses, the support staff, the health of the patients, the number of patients, the product/supply inventory, the personal protective equipment inventory, the equipment inventory, and many others. There are also complicated interaction effects. What happens if multiple patients need similar diagnostics or treatments at the same time? When taken together, all of these factors cause stress and risk for all of the stakeholders. This risk includes everything from supplies being wasted and high-risk medications being left out, to patients dying. The stakes are as high as any organization in the world because they include money and health.

It is helpful to analyze three critical components to the current problem.

One, the injuries, illnesses, traumas or incidents that an ER encounters are unique and very difficult to predict. Life happens. As a result, people are injured, get sick or incur other health problems. These are as varied as the population. For example: how many different types of injuries or wounds are possible from an automobile accident? These could range from cuts and bruises to broken backs and severed bodies. These injuries can be external (those that can be readily observed) and/or internal (those that require additional diagnostics and imaging). This incredible range of potential injuries requires hospitals and ERs to have a broad range of assets and resources available for treatment. These include people (doctors, nurses, and multidisciplinary staff), facilities (rooms, buildings, etc.), equipment (machines and devices), and supplies (bandages, syringes, scalpels, etc.).

Two, the people or Human Resources (HR) of an ER or trauma center is a significant variable. Hospitals make staffing decisions based on the desired quality of care and real-world economics. Although having an ER with 20 skilled doctors 24/7 might be ideal for patient care, it would be incredibly expensive and inefficient. Hospitals make their staffing decisions based on historical norms and predictions. Unfortunately, much like investing, past performance is no guarantee of future results. Digging deeper, even the characteristics of each staff member are important considerations. Doctors, nurses, and other hospital workers are people. This means that they have unique knowledge, skills, biases, and prejudices. One only needs to observe an ER for a few minutes to get a sense of this dynamic. For example, different doctors prefer different equipment or supplies. They may be more accustomed to one product or perhaps they believe one type of supply is better. These are variables that can be learned by the staff. A nurse may know that Dr. Smith prefers a certain size scalpel or dose of medication. This informal and unrecorded knowledge makes the ER work more effectively. The problem is that staff is constantly changing, and this knowledge is lost when the people with specific knowledge sets are either away from the ER or leave to work at other facilities. This leads to frustration among the staff as the doctor does not want to explain herself and the nurse does not want to ask questions or make incorrect assumptions. This communication problem is real.

Three, the supplies and equipment in an ER are numerous and complicated. The idiosyncrasies of needle types, bandages, or drugs are immense and potentially confusing. Large quantities of instruments, tools, supplies, and items needed in the fast-pace ERs must be stored in convenient and accessible locations. There is currently no effective way to keep track of the items used in a trauma or code. Additionally, it is difficult to have staff find the needed items fast enough. This is even worse when the nurse is unfamiliar with an item, the item was not restocked, the item was moved, or the storage location of the item is unknown. Valuable time is often wasted in codes and traumas due to attempting to find unknown items or items that have been moved or not restocked. There is no way to assess all of the items used in codes or traumas during the events. Valuable time is often wasted attempting to find movable storage carts for specific procedures. All of this searching takes precious time away from caring for critical and high-acuity patients.

The chance for human error increases under the pressure of active codes and trauma patients. Unfortunately, these errors lead to real consequences—including wasted supplies, higher costs, injury or death, and ultimately legal liability for the hospital.

These three problems with ERs are interconnected. Case in point: having unpredictable injuries enter the ER may result in a critical shortage of equipment and supplies necessary for proper diagnosis or treatment; having new staff pairings may result in understocked supplies since the hospital did not know the preferred type of supply used by a specific doctor; and having unorganized supplies and equipment may require greater staffing for searching, stocking, or organizing.

The management of an ER and its resources is complicated. One persistent issue is how to help ERs with equipment, supplies and inventory. In terms of equipment, hospitals generally purchase the equipment necessary for their location and the type of injuries/incidents that they commonly witness. These might include heart monitors, ultrasound machines, portable x-rays, and many other devices. These machines are typically stand-alone products. In other words, the individual devices are not generally connected to each other or perhaps even a larger hospital network. The machines are presently managed through hospital inventory management—likely including serial numbers and barcodes. While this is useful, there is a large amount of potentially useful data that is not recorded. This might include the number of times a machine is used, where the machine is located within the hospital or even within a room, and what order the machine was used in vis-à-vis other equipment in the room. While individual machines may be "smart," they do not interact with other machines so their usefulness is limited.

In term of supplies and other items used in the ER, there are storage companies that are geared for hospital customers. These companies generally focus on existing and well-known solutions such as shelving, cabinets, drawers, and bins. While these are useful, their effectiveness is limited by their proper installation and use.

Let us examine an analogous scenario. Imagine a set of parents buying a closet organization system for their early-teenage son. The closet includes shelves, hangers, drawers, and compartments for ideal organization—especially suited to the teen's belongings. Realistically, the teen may still throw his clothes on the floor and have his papers and possessions spread out across his desk and bed. In a pinch, the student may not be able to find his shoes in time to catch the school bus.

The described situation with the student and his closet is many times more complicated in an ER. Instead of one person, there are perhaps dozens of people working in a confined space. There is also not a lot of time for proper organization. For example: If a patient is dying, does the nurse care that the bandage bin was put back on the wrong shelf? The number of items to be organized and managed is also much more advanced. Picking the wrong colored socks doesn't matter but the wrong needle or catheter could be perilous. Even after a traumatic event, there is little time for proper organization. Current storage companies focus on maximizing vertical space but there is limited coordination with hospital and patient management.

The only real advances in product storage and dispensing for hospitals have occurred with medications and pharmaceutical drugs. There are secure dispensing systems including PYXIS™ automated dispensing cabinets by Becton, Dickinson and Company for these small items. Although some work has been done with hospital supplies, the medication cabinets are the only tightly controlled storage centers in most hospitals. This is partly a function of government and hospital regulations regarding controlled substances and other potentially dangerous medications.

Perhaps the biggest issue with current ER storage and inventory management is that it has not changed in decades. Even with the most advanced heart monitors in the world, if a nurse cannot find the tape to place an electrode, the patient's care suffers along with the reputation of the hospital. There are no specific solutions or companies for artificial intelligence, machine learning, and smart storage for the emergency departments including trauma rooms.

The present invention provides a way to utilize modern technology and software to help mitigate these real challenges.

SUMMARY

In one embodiment the inventory tracking and management system includes storage devices comprising carts, cabinets, or shelves, sensors and/or monitoring devices associated with the storage devices, a central database connecting the storage devices, sensors, and monitoring devices within a hospital, and a processing server associated with the central database. The processing server including a software system controlling operation of the inventory tracking and management system.

In some embodiments the carts are movable carts.

In some embodiments the movable carts include tracking hardware.

In some embodiments at least one of the movable carts includes a digital ID and transmitting technology.

In some embodiments at least one of the movable carts is registered in the central database for inventory.

In some embodiments at least one of the movable carts is provided with a programmable visual indicator and a sound alarm for location identification and protection.

In some embodiments at least one of the movable carts is provided with a location detection sensor and a movement sensor.

In some embodiments the central database is connected to in-patient placement, medical equipment, hospital rooms, patients, procurement services, insurance billing payment, audit quality control, computer terminals, tablets and phones, outside services, and visitors.

In some embodiments the storage devices, sensors, and monitoring devices are connected to the central database via a wireless network.

In some embodiments the monitoring devices comprise cameras providing the central database with information via the wireless network.

In some embodiments at least one of the storage devices is provided with LEDs that indicate status.

In some embodiments at least one of the storage devices includes small speakers to generate noises.

In some embodiments at least one of the storage devices includes a vibrating device signaling proper or improper movement or use.

In some embodiments at least one of the storage devices includes covers or doors including locks with passcodes or biometric protection or a means for reading name badges or IDs.

In some embodiments at least one of the storage devices includes a weight sensor to determine inventory levels and/or incorrect product placement.

In some embodiments the sensors include light or laser sensors that forwards data to the central database and processing server for the purpose of determining the occupancy of the storage devices.

In some embodiments at least one of the storage devices includes cameras monitoring contents of the storage device and sending images to the central database and the processing server which compares obtained images to known images to identify any aberrations.

In some embodiments at least one of the storage devices includes a motion sensor providing data to the central database and the processing server used to detect movement.

In some embodiments the processing server also automatically keeps track of supplies and inventory levels.

In some embodiments built-in individualized storage maps to ER/Trauma settings are provided so medical staff will know which storage unit needs to be restocked or where to find items.

Other advantages of the present invention will become apparent from the following detailed description when viewed in conjunction with the accompanying drawings, which set forth certain embodiments of the invention.

BRIEF DESCRIPTION OF THE DRAWINGS

FIGS. 12 and 13 show an alternate cabinet in a detailed view (wherein a glass door allows for viewing of the internal structure of the cabinet) and as the cabinet might be seen in use, respectively.

FIGS. 16A to 16I are exemplary supply lists.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

With reference to the various figures, the present invention provides an AI-enabled ER inventory tracking and management system 10 composed of sensors, monitoring devices, and smart software systems for ERs and trauma centers that greatly enhance health care services. As will be appreciated based upon the following disclosure, the ER inventory tracking and management system 10 of the present invention is able to keep track of all items in the emergency department storage rooms, moving carts, room carts, and trauma rooms. The ER inventory tracking and management system 10 sends immediate alerts to hospital personnel and outside vendors when items are out of stock—especially critical items.

The ER inventory tracking and management system 10 employs software based upon Artificial Intelligence (AI) and machine learning solutions to determine the urgency of a specific need. In accordance with an embodiment of the present invention, this is done using a database of inventory items along with coding as to the priority of each. The hospital environment is well-suited for the present inventory tracking and management system that utilizes Artificial Intelligence (AI) and machine learning solutions. AI and machine learning can reduce the number of variables, provide data at the right time/place, and ultimately offer intelligence to support human decision-making in the hospital. Although the described invention will offer benefits to the entire health care system, the first described use will be for the ER. While the term ER is used throughout out the disclosure, it is appreciated Emergency Department(s), EDs, Intensive Care Unit(s), ICU, ICUs, Trauma Room(s), Operating Room(s), OR, ORs, Hospital(s), Clinic(s), Emergency Clinics, Urgent Care and other patient treatment centers may mean the same thing and may be used interchangeably herein.

The AI and machine learning software utilizes an algorithm to further rank the item and prioritize its procurement. This formula accounts for the acuity of the product in patient care as well as logistical and financial considerations. For example, a less acute item might be sourced from a vendor taking two days in transit versus a same-day delivery of a very critical item (such as an intubation tube or a difficult airway kit). The software automatically sends an email or other electronic message to the preferred supply company or vendor. The ER inventory tracking and management system 10 utilizes both hardware and software elements. Key elements of the proposed ER inventory tracking and management system 10 are described herein.

Figure 1:
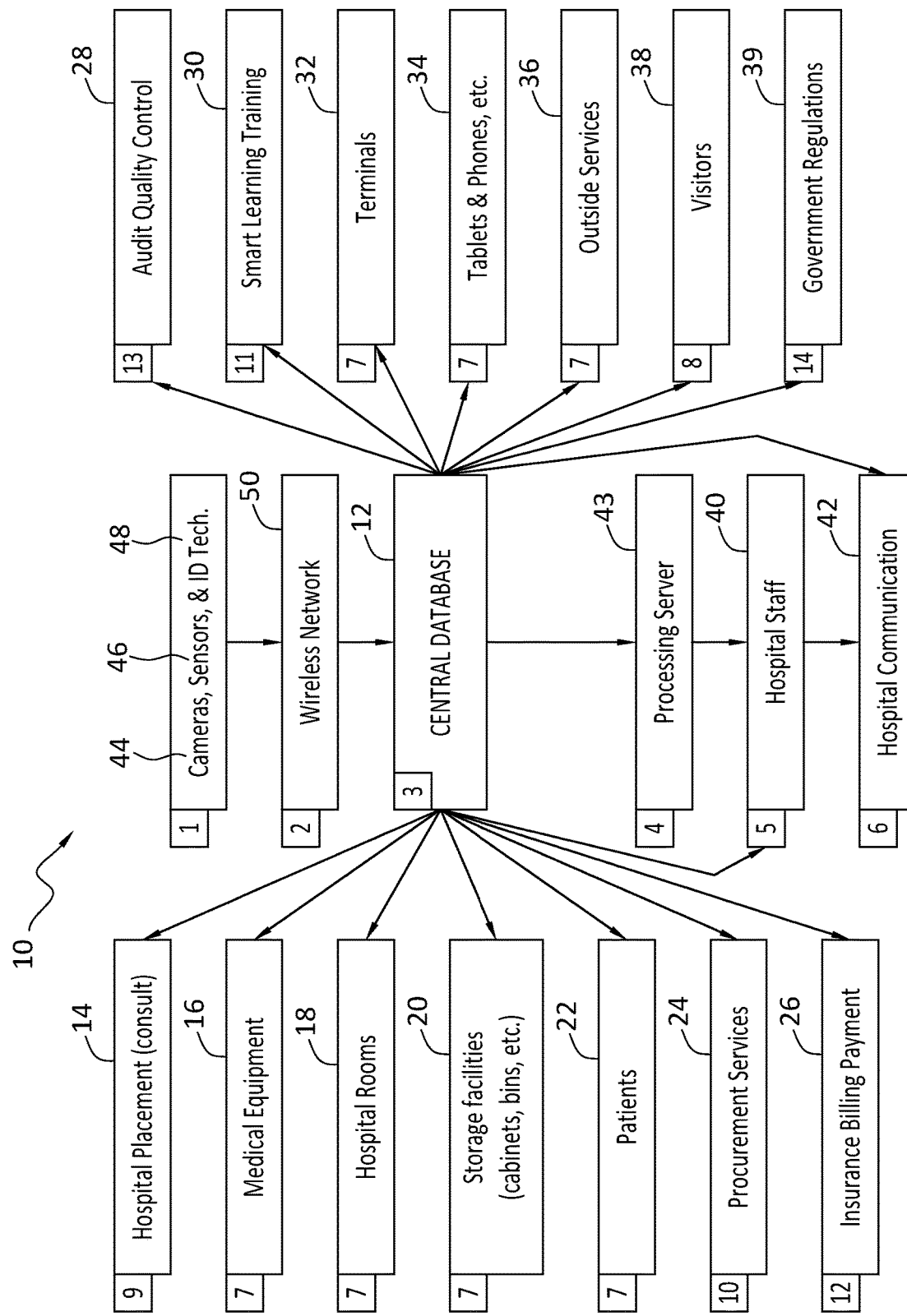
FIG. 1 is a schematic of the present ER inventory tracking and management system.
Figure 2:
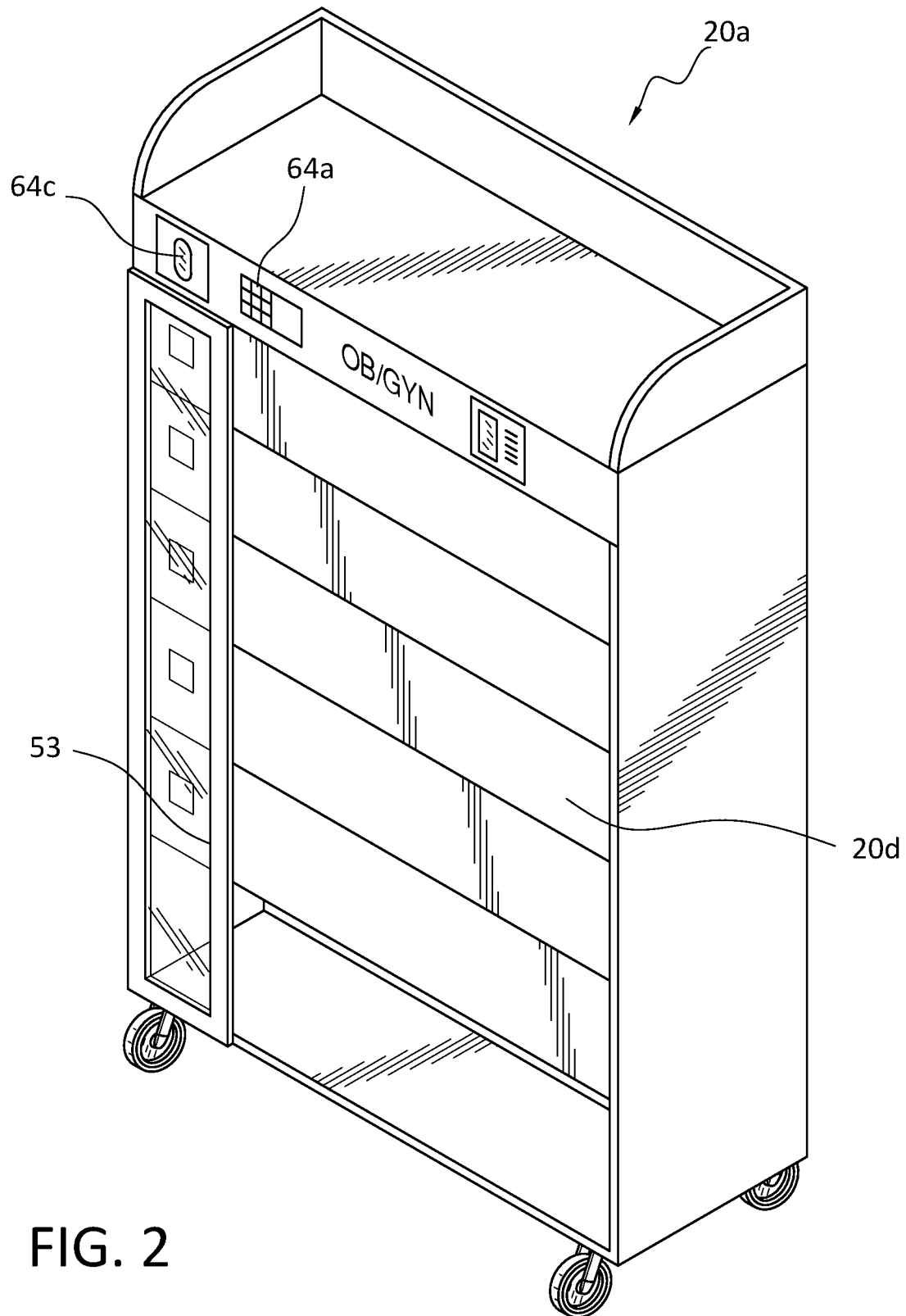
FIG. 2 is a perspective view of a movable cart with its pivotal locking panel closed.
Figure 3:
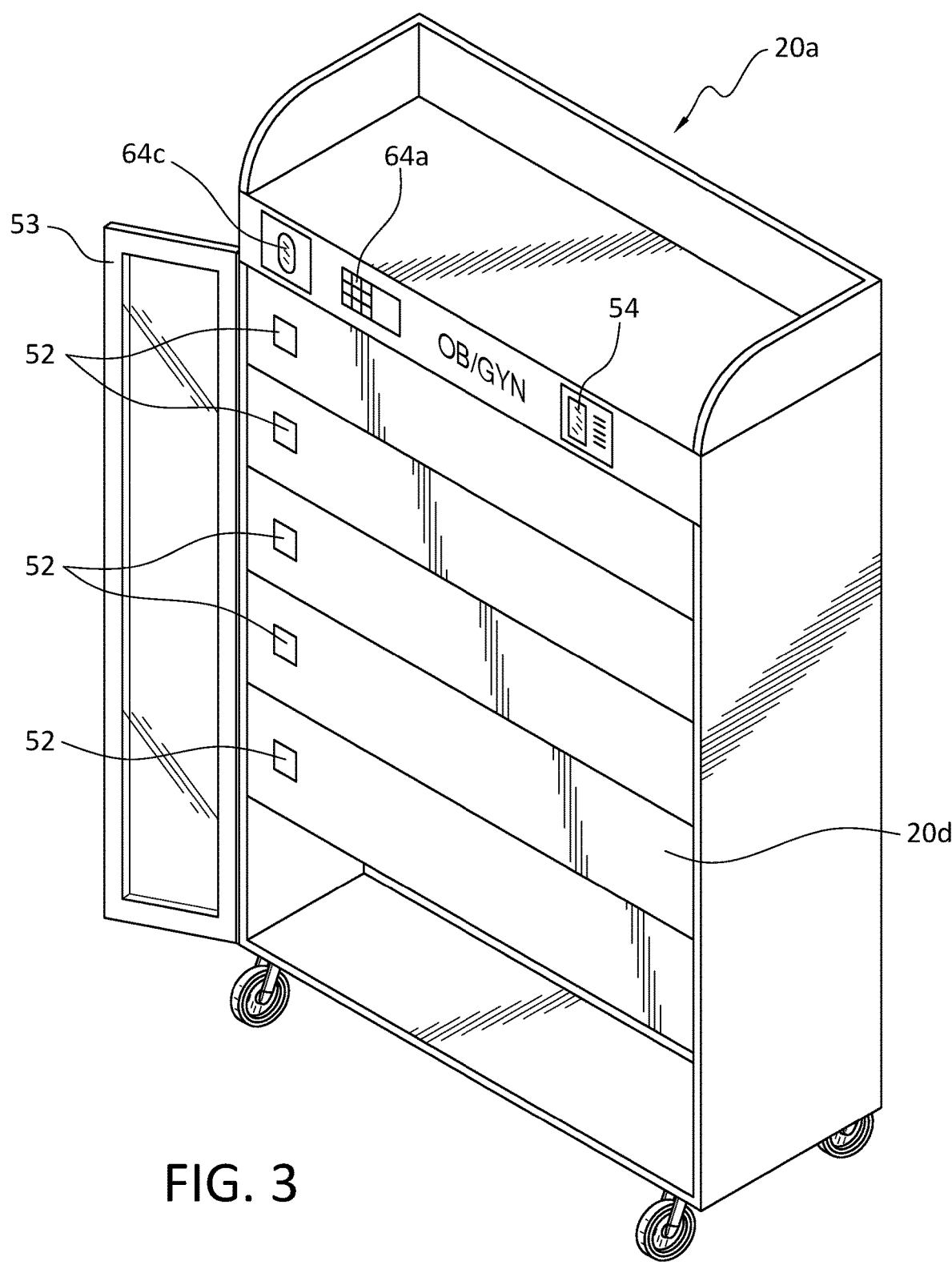
FIG. 3 is a perspective view of a movable cart with its pivotal locking panel.
Figure 4:
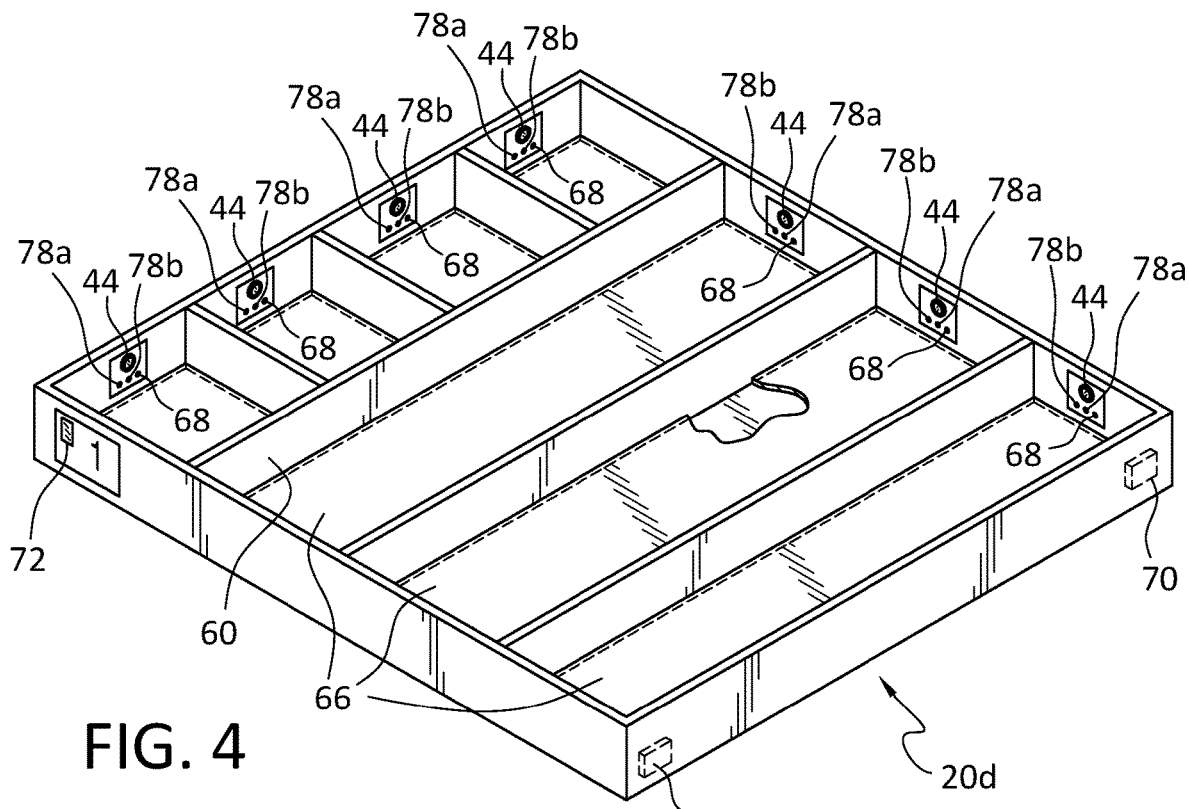
FIGS. 4 and 5 are perspective views of alternate embodiments for drawers used in conjunction with the movable cart shown in FIGS. 2 and 3.
Figure 5:
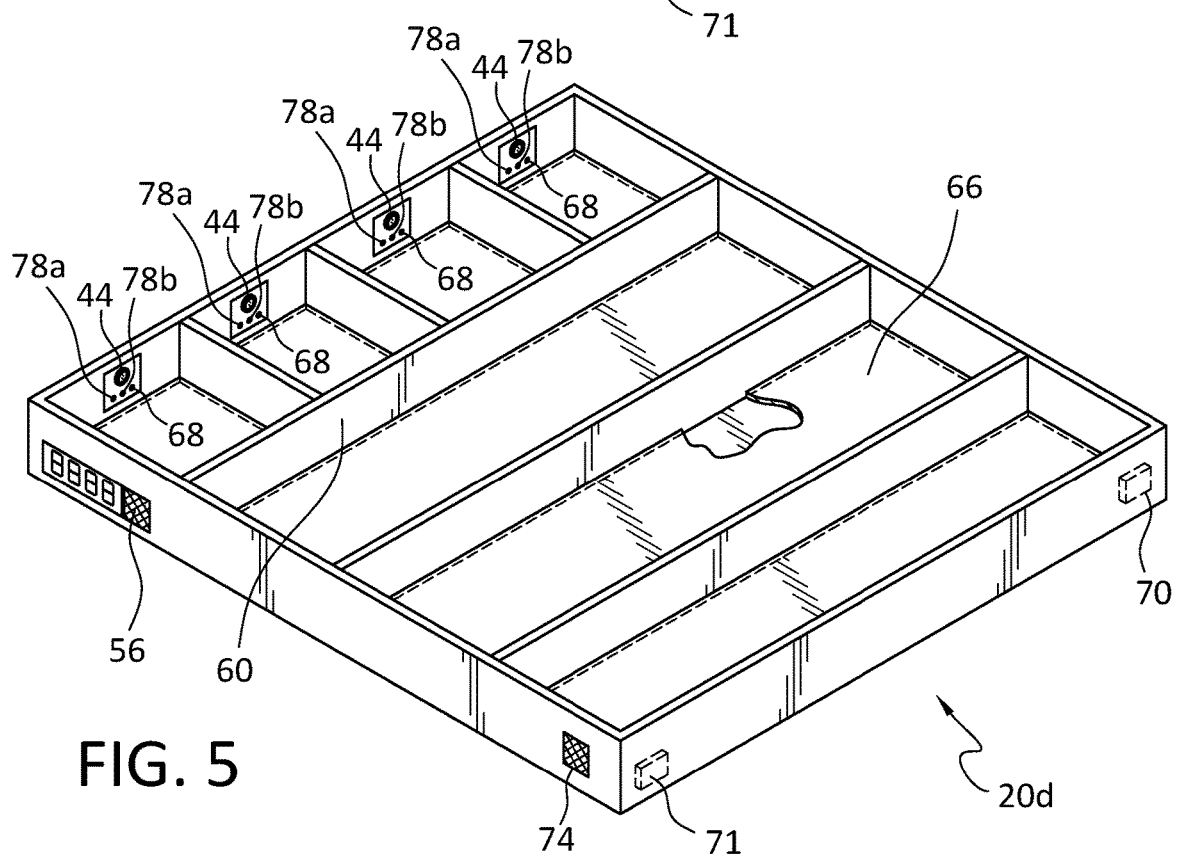

Referring to FIG. 1, a general overview of the present ER inventory tracking and management system 10 is disclosed. The ER inventory tracking and management system 10 includes a central database 12 connected to, and ultimately connecting a plurality of components found within a hospital. The central database 12 is directly connected to specific hospital sections, including but not limited to, in-patient placement (consult) 14, medical equipment 16, hospital rooms 18, storage facilities (medical carts 20a, cabinets 20b, bins 20c, etc.) 20, patients 22, procurement services 24, insurance billing payment 26, audit quality control 28, smart learning (training) 30, computer terminals 32, tablets and phones 34, outside services 36, visitors 38, and government regulations 39. The central database 12 is also connected to hospital staff 40 via known communication methods, for example text, audio, image, and video messaging via smartphones and other devices and to hospital communication systems 42. Such hospital communication systems 42 may include hospital-wide paging and other alert messaging known to those skilled in the art.

The components listed above are connected to the central database 12 via a wireless network 50 and the processing of data within the central database 12 is controlled by a processing server 43 operating under the control of the AI and machine learning software discussed above. The hospital staff 40 receives information from the processing server 43. While this is preferred method, other methods may be employed in the spirit of this invention.

Further still, and as will be appreciated based upon the following disclosure, the present ER inventory tracking and management system 10 is replete with cameras 44, sensors 46, and identification technology 48 that provide the central database 12 with information via the wireless network 50 and any other networks that might be integrated into the hospital.

As mentioned above, and with reference to FIGS. 2, 3, 4, and 5, the ER inventory tracking and management system 10 makes use of movable carts 20a with removable or withdrawable drawers 20d. It should be noted that the disclosed drawers 20d are associated with the movable carts 20a and specific references to structure that might be included with the drawers 20d should be indicative that the movable carts 20a also includes such structure. However, it is also appreciated the drawers could be used in conjunction with other storage structures separate and apart from the movable carts. In accordance with the present invention, the ER inventory tracking and management system 10 provides for tracking of the movable carts 20a for procedures, so nurses and other staff do not have to waste time walking into multiple rooms trying to find the items they need. The carts 20a are provided with tracking hardware known to those skilled in the art. For example, the carts 20a could be enabled with a digital ID and transmitting technology 52 such as an antenna, RFID (radio-frequency identification), NFC (near-field communication), or Bluetooth. Access to the transmitting technology 52, as well as the drawers 20*d* of the carts 20*a*, is controlled by a pivotal locking panel 53 positioned along an edge of the cart 20 such that it may be opened and closed to control access to the transmitting technology 52 and the drawers 20*d*. While a pivotal locking panel is shown in conjunction with a disclosed embodiment, it is appreciated the locking panel may take the form of a standard lockable door. It is anticipated the tracking technology employed in accordance with the present invention might include various locating means, including, but not limited to, GPS (global positioning system), cellular signal triangulation, and other known methods.

The drawers 20*d* and pivotal locking panel 53 of the cart 20*a* may are preferably lockable. In accordance with a disclosed embodiment, the locks are passcode code-based locks 64*a* or locking mechanisms employing technology to read name badges or IDs 64*b*. The locking features may also be engaged/disengaged via biometric inputs such as fingerprints, iris scans or facial recognition. The locks may also be programmed to unlock when in proximity to the proper personnel—achieved through a recognition of their badge, smartphone or their photographic image. However, it is appreciated a variety of electronic and mechanical locking mechanisms are known in the art and may be used in conjunction herewith.

Each cart 20*a* is registered in the central database 12 for inventory. Each time the carts 20*a* are cleaned, serviced, restocked, or used, they are scanned and the updated data is stored—either on the carts 20*a* or in the central database 12, or on both.

The ER inventory tracking and management system 10 might also include location detection and movement sensors, for example, cameras 44, spread throughout the hospital (as shown with to the various figures showing elements of the present system). In addition to monitoring a wide variety objects and people within the hospital, the cameras 44 are integrated into the carts 20*a* and enhance the monitoring of the location of carts 20*a* moving throughout the hospital and continually send such information to central database 12 for ready access by individuals needing to know the location of the many carts 20*a* scattered through a hospital (for example, see the cameras 44 in the cart drawers 20*d* as shown with reference to FIGS. 4 and 5). In this way, the hospital, and its staff, always knows the location of its carts 20*a*. Furthermore, the carts 20*a* are provided with programmable visual indicators (such as LEDs) 54 and sound alarms 56 for location identification and protection, for example, providing time and quantity information regarding patient dosing. Such timing might be controlled by starting the timer once a drawer (or tray) is taken out of the cart 20*a*.

Moveable carts are presented in accordance with a disclosed embodiment. However, it is appreciated moveable carts take a variety of forms and the concepts underlying the present invention may be applied to hospital carts that may come in the future and currently existing carts, such as for example, TouchPoint Mobile Technology Carts from HUMANSCALE®.

Figure 6:
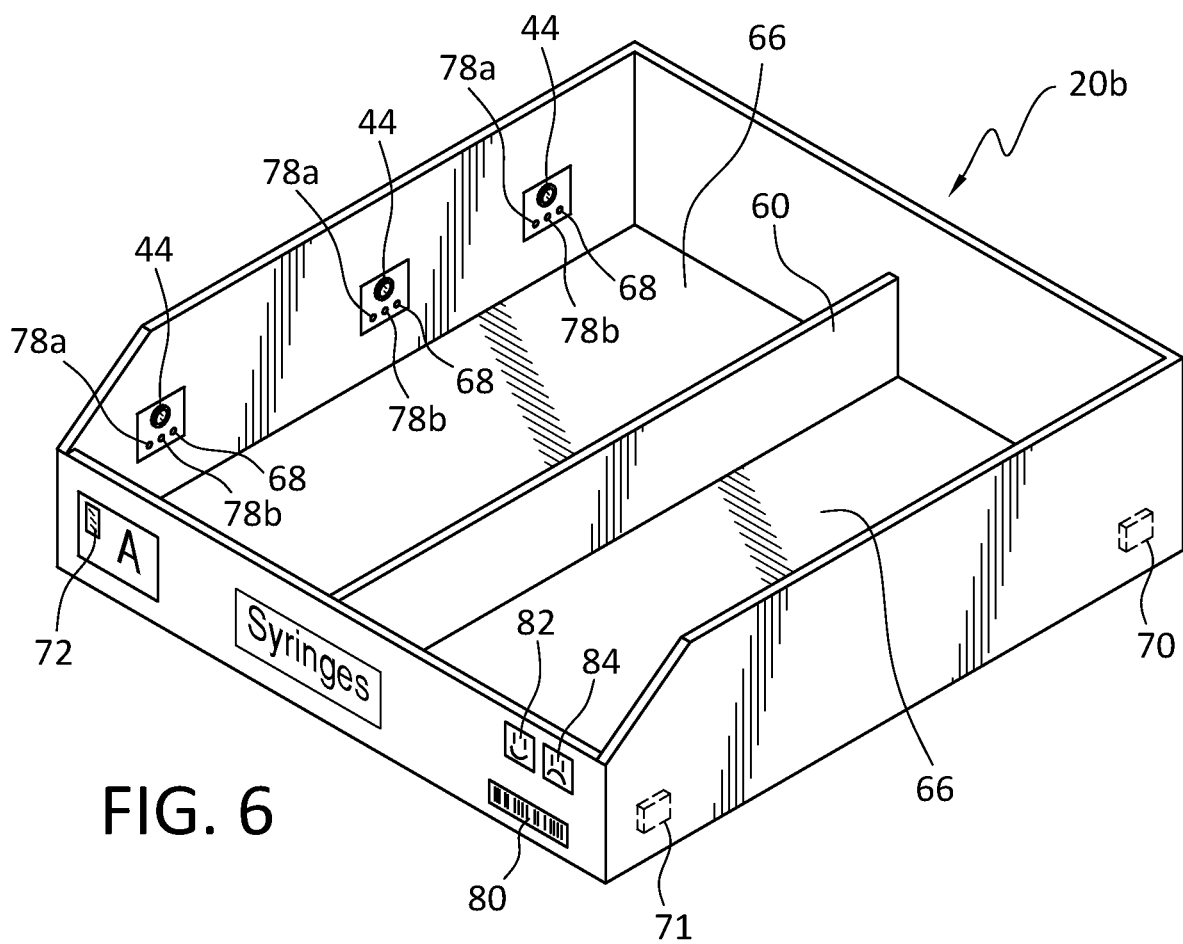
FIG. 6 is a perspective view of a bin.
Figure 7:
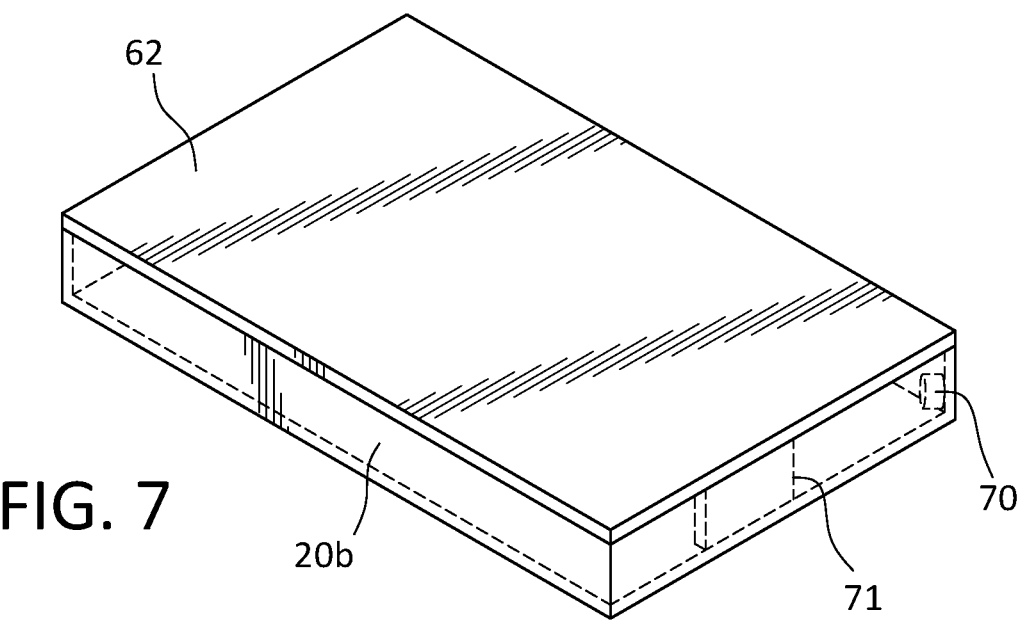
FIG. 7 is a perspective view of a bin with a closed cover.
Figure 8:
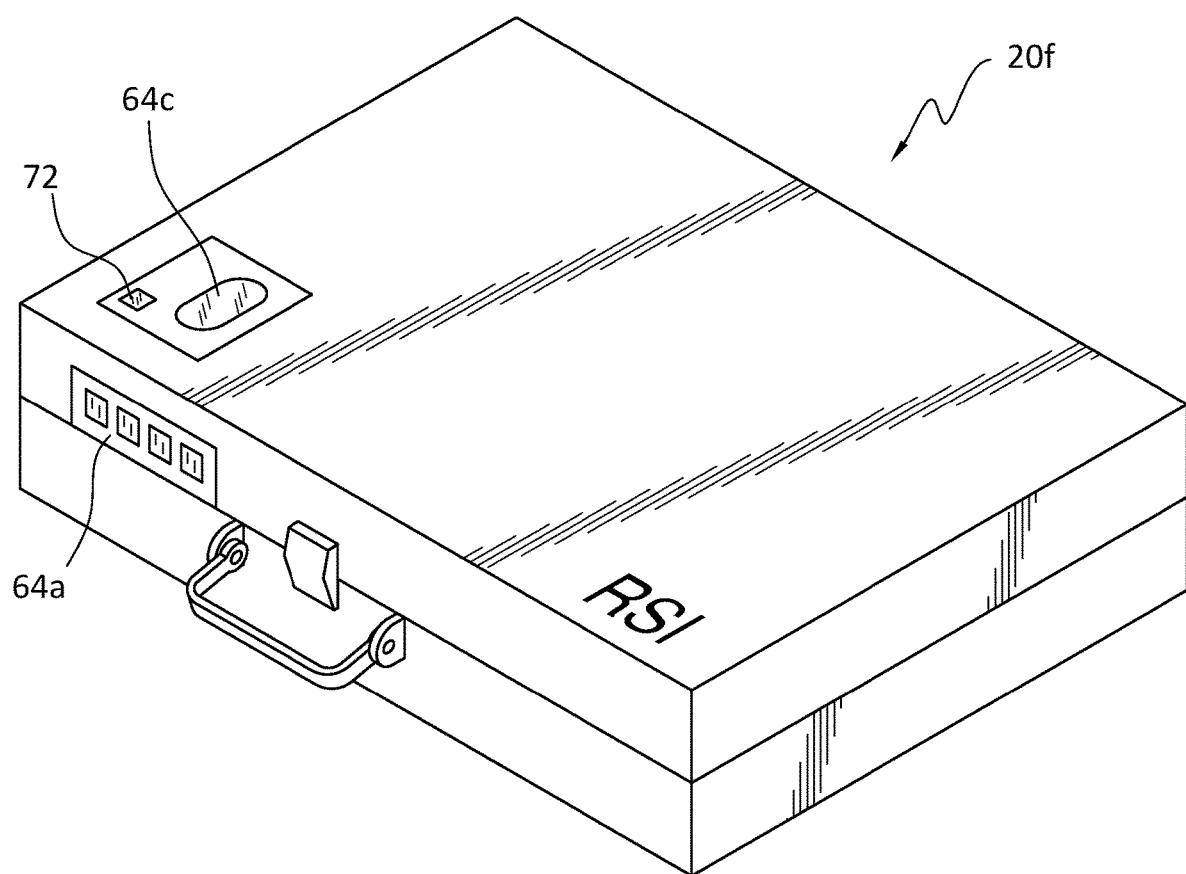
FIGS. 8 and 9 are perspective views of rapid sequence induction (RSI) kits in closed and open configurations, respectively.
Figure 9:
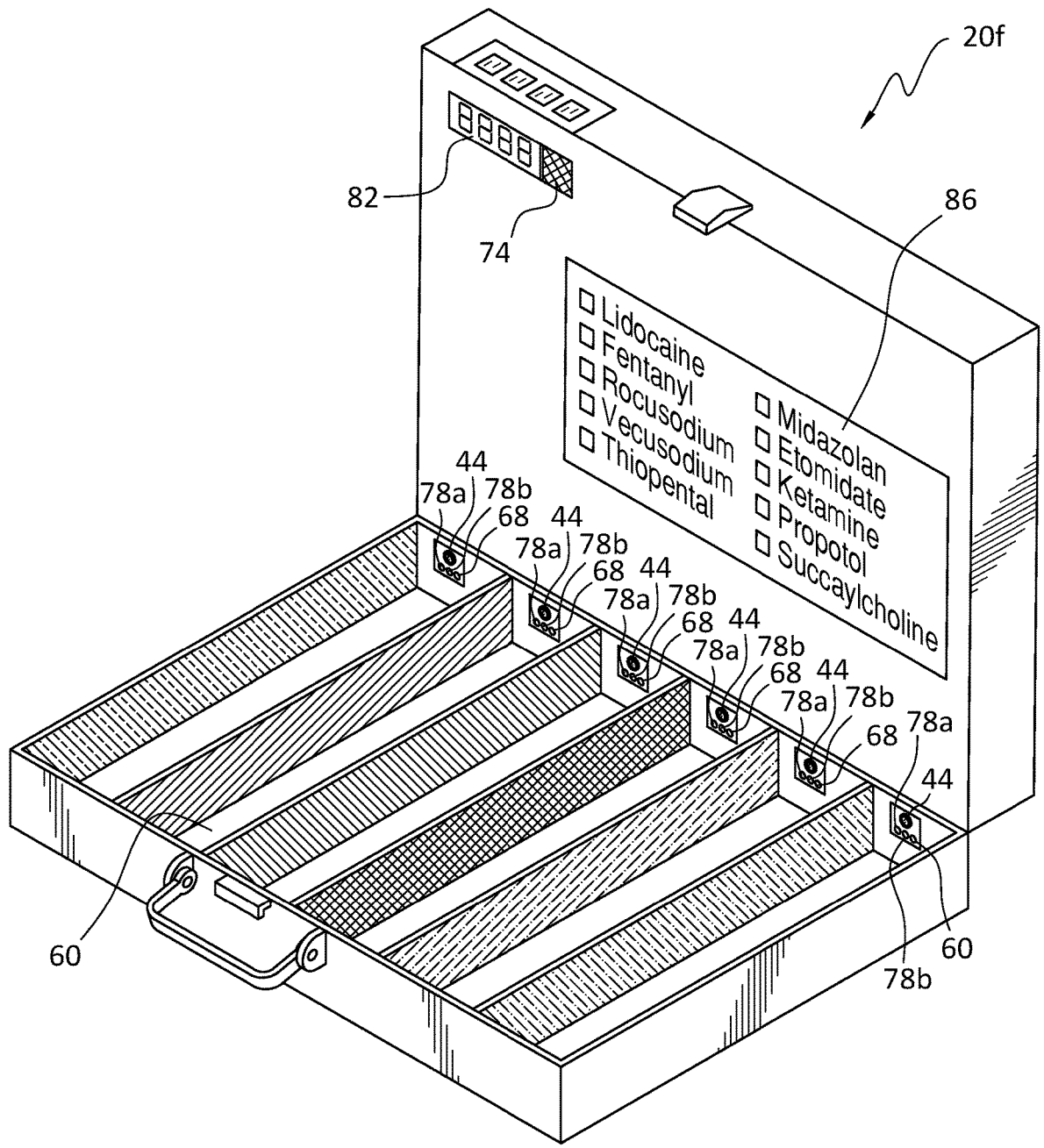
Figure 10:
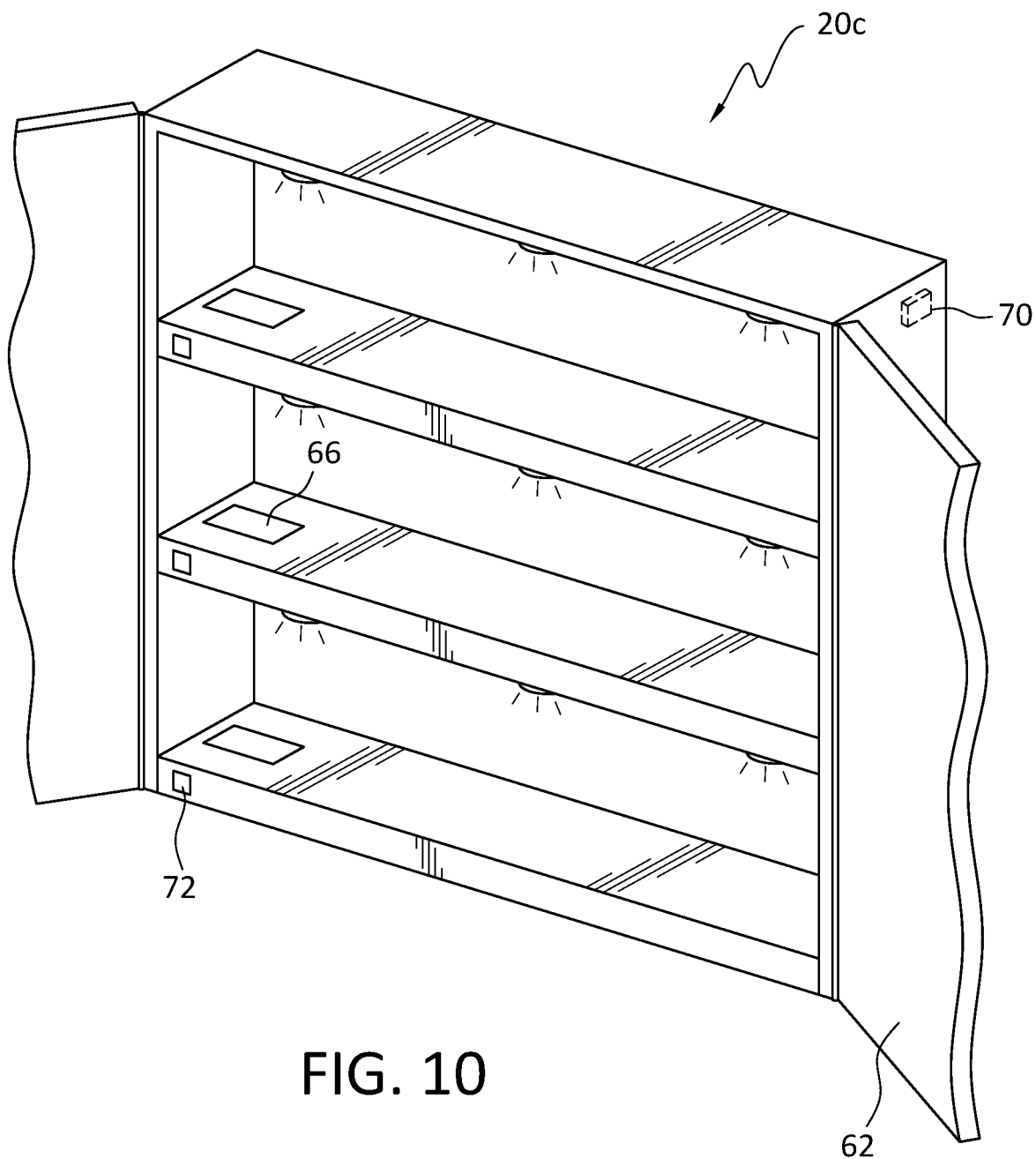
FIGS. 10 and 11 show a cabinet in open and closed configurations, respectively.
Figure 11:
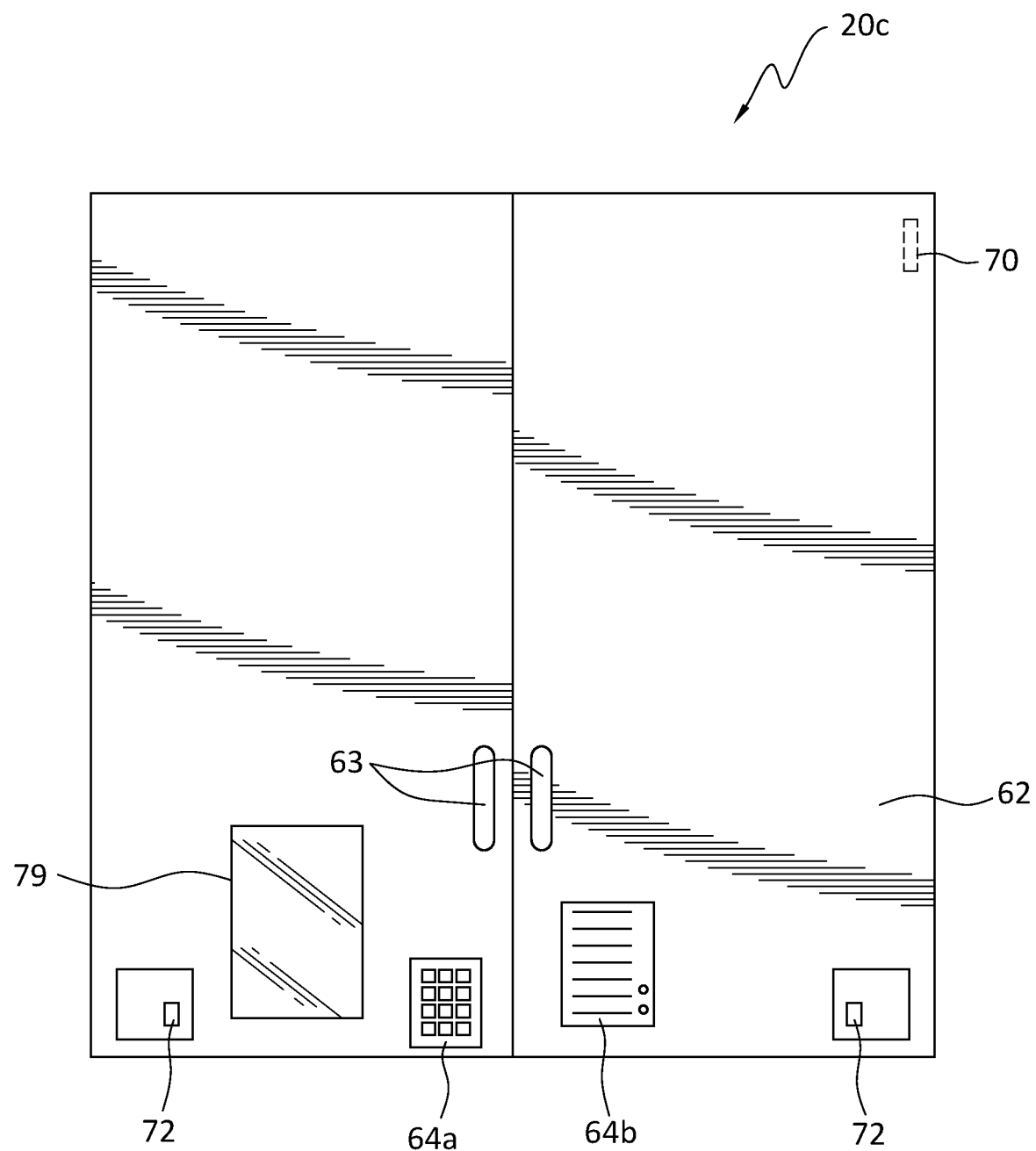

The ER inventory tracking and management system 10 also anticipates various storage solutions. These solutions include bins 20*b* (see FIGS. 6 and 7), baskets, boxes, drawers 20*d* (for example, of the carts 20*a* disclosed above), kits 20*f* (for example (rapid sequence induction (RSI) kits as shown in FIGS. 8 and 9), cabinets 20*c* (see FIGS. 10, 11, 12, and 13), shelves (for example, roll out shelves) 20*e* (see FIG. 12), and other storage products, all of which are linked to the central database 12 with information relating thereto readily available for hospital staff requiring information regarding their content, usage, status, or other information that might be needed. It is appreciated that while specific functional components might be discussed herein in conjunction with a specific type of storage solutions, the functional components may be used in conjunction with any of storage solution found within a hospital. In addition, various embodiments are disclosed herein and similar references numerals are used where the structure is similar.

The shape and construction of these storage solutions may be unique for enhanced functionality. These storage products may have unique designs and functions. The storage products may be constructed from various materials. These materials may include steel, aluminum, magnesium, titanium, polymers, plastics, or alternate materials. The materials should be suited for longevity and durability. They should also be sanitizable and/or be made with anti-microbial materials. It is also anticipated that unique micro-surface textures might be employed on the storage products. These might include patterns inspired by shark skin or other natural surfaces that repel microbial growth. The storage products can be sized to accommodate various products and for various uses. These storage solutions may also be modular and interconnectable to allow for hospital-specific customization. The storage solutions may also have internal compartments, dividers, or other means of segmentation or organization 60.

The cabinets 20*c* may also have covers or doors 62 (with handles 63). In accordance with a disclosed embodiment, these covers or doors 62 are lockable. These locks could be mechanical with a key or keypad or they may be electronic (for example, as shown with reference to 64*a*, 64*b*, and 64*c*). The electronic versions may include passcode-based locks 64*a*, biometric protection (such as fingerprint, iris scan) 64*c* or locks including mechanisms to read name badges or IDs 64*b*. Proximity by authorized personnel might also allow immediate unlocking based on electronic signals or image recognition obtained from the cameras, scanners or sensors in the room. Similarly, and were appropriate, the carts and/or bins may be provided with lockable doors such as disclosed above with regard to the cabinets.

The storage products also include location tracking devices. With respect to security, some of the bins 20*b* and/or cabinets 20*c* (as well as the carts 20*a* as discussed above) may also automatically be track and be locked after use to prevent their opening or multiple removals. All of these enhanced security features may be managed through administrative software running on the processing server 43. The administrative software of the processing server 43 allows for customization and access preferences. This customization preferably includes levels of access or priority within the hospital. For example, each nurse might be limited in his or her access to drawers or bins with specific items (for example pain killer medications). This access could also be administered in smart fashion. This would allow for drawers or bins to open to certain personnel upon the receipt of an incoming emergency. For instance, the drawer with the rapid sequence intubation kit might normally be locked but would open once a proper incoming emergency was registered in the system.

The bins 20*b*, drawers 20*d* (for example, of the carts 20*a* disclosed above), and/or cabinets 20*c* may also employ various technologies to identify and track their contents. For example, some of the bins 20*b*, drawer 20*d* and/or cabinets 20*c* include a weight sensor 66 at the bottom of the bins 20*b*, drawers 20*d*, and/or cabinets 20*c*. This sensor 66 records and sends the current weight of object within the bins 20b, drawers 20d, and/or cabinets 20c to the central database 12 of the ER inventory tracking and management system 10. This information is compared to known weights by the processing server 43 to determine inventory levels and/or incorrect product placement. In addition to weight, pressure sensors might also be employed that account for weight but also displacement and distribution of mass.

The ER inventory tracking and management system 10 also includes light or laser sensors 68 that forward data to the central database 12 and processing server 43 for the purpose of determining the occupancy of the bins 20b, drawers 20d (for example, of the carts 20a disclosed above), and/or cabinets 20c based on the reflection of the lights within the bins 20b, drawers 20d, and/or cabinets 20c. The light or laser sensors 68 communicate with the central database 12 and processing server 43. The central database 12 contains items organized by their dimensions including height, length, and width along with weight and mass numbers. Furthermore, items may be stored based on their defining visual features that could be analyzed with machine learning software.

The bins 20b, drawers 20d (for example, of the carts 20a disclosed above), and/or cabinets 20c also include cameras 44. The cameras 44 monitor the contents of the bins 20b, drawers 20d, and/or cabinets 20c and send images to the central database 12 and the processing server 43 which compares obtained images to known images to identify any aberrations. These aberrations might indicate incorrect inventory placement or low inventory levels. For example, if a scissors were placed in a bin with bandages, the camera 44 (and/or other sensor) would recognize that the scissors does not look like the normal inventory consisting of bandages and tape. This recognition would then trigger a series of calculations and potential alerts ideally without or with limited human interaction. The image recognition software would be highly advanced so that it could zoom in on product details to distinguish between unique product variations. For example, the camera could discover branding or product numbers engraved on metal items or labels on packaging.

The bins 20b, drawers 20d (for example, of the carts 20a disclosed above), and/or cabinets 20c also include motion sensors 70. The motion sensors provide data to the central database 12 and the processing server 43 used to detect movement within the bins 20b, drawers 20d, and/or cabinets 20c or movement of the bins 20b, drawers 20d, and/or cabinets 20c itself. Through the use of the cameras 44 and other monitoring systems, the central database 12 is able to gather information that is then used by the processing server 43 to notify staff when high-risk medications are being left unattended or left out. These motion sensors may also trigger lighting so the proper items or areas are illuminated during use.

Figure 14:
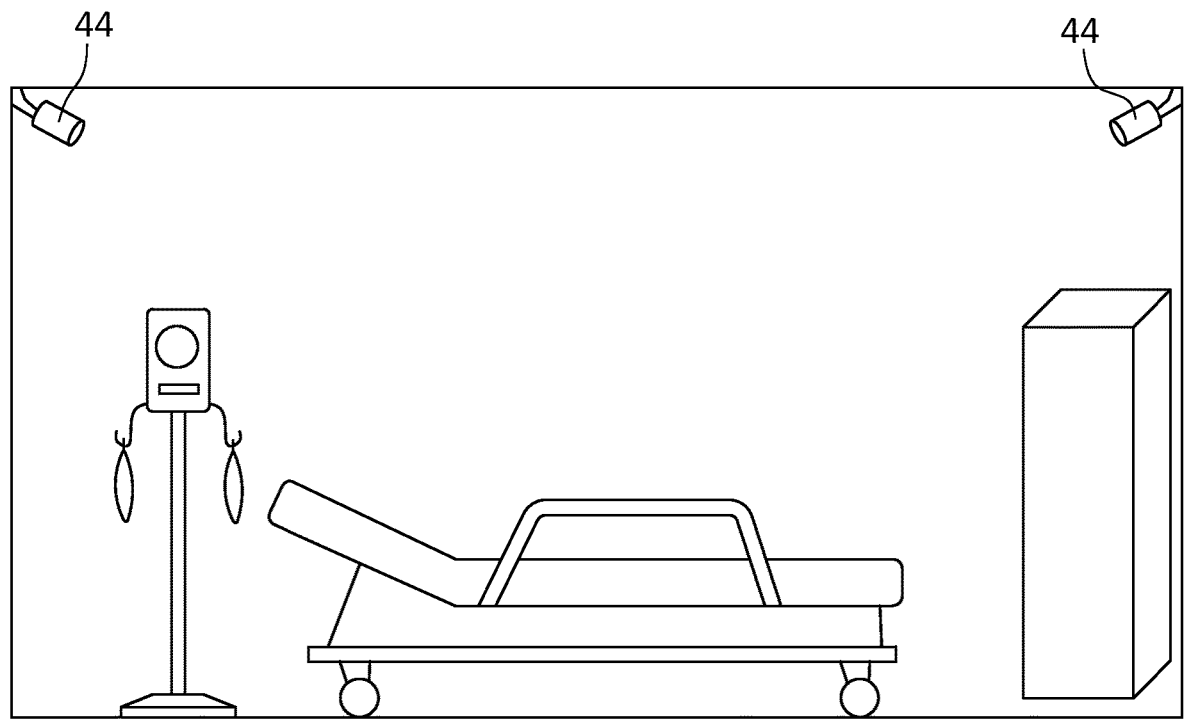
FIG. 14 is a schematic of a hospital room.

As mentioned above, the ER inventory tracking and management system 10 makes use of location detection and movement sensors, for example, including cameras 44, spread throughout the hospital (see FIG. 14 showing a hospital room with cameras 44). The data obtained from the cameras 44, and other detection mechanisms, is utilized in conjunction with object recognition running on the processing server 43, which accesses the monitoring data maintained on the central database 12 to identify relevant information. As part of the identification process associated with the use of cameras 44, and other location detection devices and movement sensors, the central database 12 includes a digital library with pictures and images pertaining to the items and supplies used in the ER. These items are easily identified with the photo and data on the screen of a monitor, tablet, or smartphone. In accordance with a preferred embodiment, the cameras 44 capture images at set intervals and/or through constant monitoring. At initiation of the ER inventory tracking and management system 10, the processing server 43 is trained to "know" various objects. This setup is achieved using human supervision or help with identification—including processes like Mechanical Turk from Amazon (which is a crowdsourcing website to hire remotely located worker" to perform discrete on-demand tasks). Furthermore, the software would use measurement characteristics and geometric computations to help identify products. Similar to facial recognition software, this processing could look for shapes, patterns and key features to help make correct identifications. This allows the ER inventory tracking and management system 10 to notify the hospital or its personnel when items are missing or other aberrations have occurred. This capability also assists in inventory management and ensures proper supplies and equipment are available when needed.

The bins 20b, drawers 20d (for example, of the carts 20a disclosed above), and/or cabinets 20c transmit their data to the central database 12 where everything is managed—in part through machine learning and autonomous technologies. In addition to the transmission of the data, the bins 20b, drawers 20d, and/or cabinets 20c are also provided with physical indicators allowing for quick staff assessment. These physical indicators, include, but are not limited to, lights, sounds and vibrations. For example, the bins 20b, drawers 20d, and/or cabinets 20c may include LEDs 72 that may be colored green, yellow and red to indicate their status. The lights could also be incorporated in the construction of the bins 20b, drawers 20d, and/or cabinets 20c. The bins 20b, drawers 20d, and/or cabinets 20c might also include small speakers 74 to generate noises that may include alarms or voice commands. The bins 20b, drawers 20d, and/or cabinets 20c may also include lights 78a, 78b indicating proper/improper placement of items within the bins 20b, drawers 20d, and/or cabinets 20c or providing pre-defined suggestions relating to the contents of the bins 20b, drawers 20d, and/or cabinets 20c. The bins 20b, drawers 20d, and/or cabinets 20c may also contain a vibration device 71 that signals proper or improper movement or use. Further still, and with reference to the cabinet 20c shown in FIG. 11, touch screens 79 may be employed to ease the use of the various storage devices and to provide information to those using the storage devices.

With regard to the bins 20b, they are designed for use in a variety of locations and, therefore, may be provided in different shapes, sizes and colors, with the ability to be hung on peg board, for sitting upon a shelf, in a manner allowing for stacking, with dividers that may or may not be adjustable, and for ease of cleaning.

As to the RSI kits 20f discussed above, these include many of the functional elements discussed above. In addition, and as shown with reference to FIG. 9, the dividers 60 within the kits 20f may be colored coded (and such color coding may be applied to other storage devices disclosed herein. The kits 20f may also include pouches for syringes, flushes, etc. (not shown) and lights (not shown) for ease of identification of medications within the kit (not shown). In addition, the lights 78a, 78b may be used to provide medical practitioners with a visual aid regarding the correct order of the medications (for example, pain agents, sedation agents, paralyzer agents, etc.). It is also possible for manufacturers to include this expiration data in their shipping messages and other electronic communications with the hospital and its procurement systems. In this way, the age of items would be known—even without a scan or analysis of the printed dates on the product.

This ER inventory tracking and management system 10 also keeps track of expiration dates of stocked items and alerts staff when items are close to expiration dates. This is achieved through the use of barcodes and/or QR codes 80 so that scanning with a reader or smartphone is possible. This facilitates easier access to supplies. It also enhances staff training and allows for simulations to train nurses and others on getting the supplies as quickly as possible.

The ER inventory tracking and management system 10 also allows for voice commands or on-screen selection 86 to find items quickly. A 3D scanning or imaging system 84 may also be employed. This would allow unknown or unfamiliar items to be placed under or near the scanner. The scanner would then scan the item and compare it to known images in the database. It could then give the user a positive identification of the product. The ER inventory tracking and management system 10 also might suggest, "if you like this, you may like . . . " or "you may also need" 82, recommendations based on machine learning and software calculations.

The ER inventory tracking and management system 10, through the use of the processing server 43, automatically generates lists of potential items that might be needed in response to incoming codes and traumas specified to individual hospital needs. The ER inventory tracking and management system 10 could even adjust these recommendations for supplies based on the specific staff in the hospital at that time. In achieving this goal, the ER inventory tracking and management system 10 "remembers" the preferences of certain doctors (based upon information input into the system during the set-up processing and the ongoing maintenance of the system) and pulls those up automatically to assist the nurses and staff on duty. Depending on the incoming incident or code, the items or the bins in which the correct supplies are located light up for quick identification and access.

This memory of various codes and incidents could also be compared across the hospital or to other hospitals. For example, perhaps the success rate of an emergency surgery is higher when once type of supply is utilized. This information could be broadly rolled out beyond the smart advice for one doctor and one ER.

The central database 12 is also linked to existing purchasing and inventory management software solutions currently utilized by hospitals. As briefly mentioned above, it is also anticipated that the software could include voice commands, recognition and interaction.

The ER inventory tracking and management system 10 through the processing server 43 also automatically keeps track of supplies and inventory levels. This is accomplished with the weight-based scales 66 discussed above to keep track of used items. Pressure sensors and light sensors are also used to advise the ER inventory tracking and management system 10 when items have been removed or misplaced based on size. It is also anticipated that cameras 44 could monitor the bins 20b, drawers 20d, and/or cabinets 20c and recognize changes in the shapes and quantity of the contents of the bins 20b, drawers 20d, and/or cabinets 20c. With the foregoing in mind, and considering communication between the central database 12, the processing server 43, and the various components of the ER inventory tracking and management system 10, the ER inventory tracking and management system 10 is able to keep a running count of items used in a code or trauma for medical professionals to look back at when charting. If an item is out of stock, the ER inventory tracking and management system 10 locates the item at another location or suggests the next best substitute item that could be used. If an item is not used and is placed back in storage area, the ER inventory tracking and management system 10 recognizes the weight, location, or size of the item and restocks the item, thus removing it from the running list. All of this is linked to patient records, billing, purchasing, and general hospital management. These mechanisms would also help prevent theft or improper patient billing.

Figure 15:
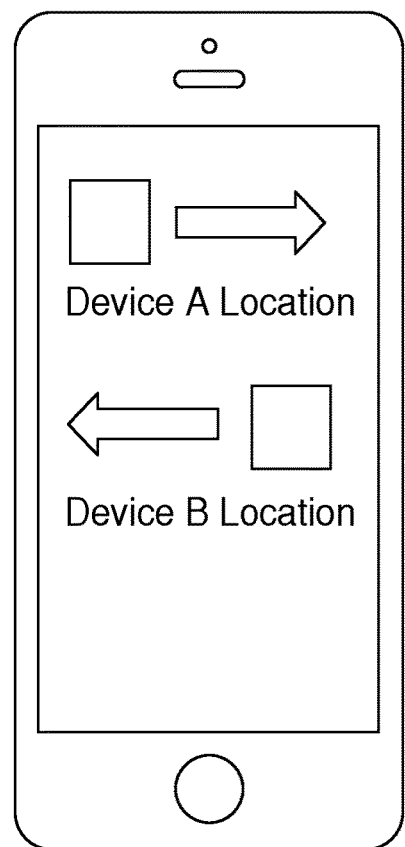
FIG. 15 shows a smartphone with a screenshot of a graphical user interface.

The ER inventory tracking and management system 10 also includes built-in individualized storage maps to ER/Trauma settings so medical staff will know which storage unit needs to be restocked or where to find items (for example, see FIG. 15 showing a smartphone with a graphical user interface providing directional information). The ER inventory tracking and management system 10 will also produce inventory lists as shown in FIGS. 16A to 16I. Once an item is requested by medical staff, the correct bin lights up (via the tracking light 72) or sounds off (via the speaker 74) to identify the location of the desired item. The light or sound alarm has a timer to turn off to save energy and minimize distraction after its use. The ER inventory tracking and management system 10 is designed to find items for medical staff to minimize time wasted on searching and maximize the critical amount of time spent saving lives. The ER inventory tracking and management system 10 is meant to further minimize human error in a high-pressure and fast-paced setting.

The ER inventory tracking and management system 10 communicates its information to users via various computer screens. These screens would utilize icons, windows and other graphical elements to effectively display the relevant data. The computer screen can take a variety of forms, including, but not limited to, smartphones, tablets, display screens, monitors, or other display means. The computer screens depict writing, graphics, and icons to facilitate user interaction. In accordance with a preferred embodiment, the computer screens are "smart" so that an action on one would update the central database 12 and the display would refresh on the other devices within the ER inventory tracking and management system 10.

The ER inventory tracking and management system 10 also has feedback mechanisms for communication between the user and supplier—including the manufacturer. For example, the bins 20b, drawers 20d, and/or cabinets 20c have satisfied and unsatisfied buttons 82, 84 to indicate user acceptance. The ER inventory tracking and management system 10 may also be more advanced and include email feedback or feedback requesting future communication or support from suppliers/partners or vendors.

The present ER inventory tracking and management system 10 is envisioned as a modular system that can be effectively scaled based on the needs of the hospital or organization. As noted above, the ER inventory tracking and management system 10 relies on modern sensors, cameras, communications, and other technologies to keep track of inventory items. The electronic components communicate their status to each other via the central database 12 and the processing server 43, wherein all of the data generated by the ER inventory tracking and management system 10 is stored in the central database. This data can be analyzed using machine learning through the implementation of known techniques. The ER inventory tracking and management system 10 then has the ability to make recommendations and flag areas for improvement. These flagged items could be as simple as waste reduction or as important as life-saving equipment location.

It is also envisioned that this ER inventory tracking and management system 10 may link with robotic technology and other autonomous hospital equipment. These might include simulators, rovers, drones, robots, and other electronic equipment designed to support medical care in the hospital.

Another advantage to the proposed invention is the potential liability reduction for the hospital and its staff. With cameras, sensors and advanced recordation, the ER inventory tracking and management system 10 provide a comprehensive record of items used and the corresponding procedures. For example, a patient who claimed he or she did not receive the proper treatment could be addressed with actual camera images and data showing the proper supplies, equipment, and personnel were involved in standard care procedures. The images and data are stored for set periods of time based on the risk profile of the incident and other factors determined by hospital administration and legal. This digital archive is valuable for outside interests such as insurance companies and government entities as well.

Those skilled in the art will appreciate that the various illustrative logical blocks, modules, circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall ER inventory tracking and management system 10. Skilled artisans may implement the described functionality in varying ways for each particular application, but such implementation decisions should not be interpreted as causing a departure from the scope of the exemplary embodiments.

The various illustrative logical blocks, modules, and circuits described in connection with the embodiments disclosed herein, may be implemented or performed with a general or specific purpose processor, or with hardware that carries out these functions, e.g., a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine.

The processor can be part of a computer system that also has an internal bus connecting to cards or other hardware, running based on a system BIOS or equivalent that contains startup and boot software, system memory which provides temporary storage for an operating system, drivers for the hardware and for application programs, disk interface which provides an interface between internal storage device(s) and the other hardware, an external peripheral controller which interfaces to external devices such as a backup storage device, and a network that connects to a hard-wired network cable such as Ethernet or may be a wireless connection such as a RF link running under a wireless protocol such as 802.11. Likewise, external bus 18 may be any of but not limited to hard wired external busses such as IEEE-1394 or USB.

The computer system can also have a user interface port that communicates with a user interface, and which receives commands entered by a user, and a video output that produces its output via any kind of video output format, e.g., VGA, DVI, HDMI, display port, or any other form. This may include laptop or desktop computers, and may also include portable computers, including cell phones, smartphones, tablets such as the IPAD™ and Android platform tablet, and all other kinds of computers and computing platforms.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module executed by a processor, using cloud computing, or in combinations, using tangible computer programming. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer-based instructions. An exemplary storage medium is coupled to the processor such that the processor can read information from, and write information to, the storage medium. In the alternative, the storage medium may be integral to the processor. The processor and the storage medium may reside in reconfigurable logic of any type.

Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and Blu-Ray disc where disks usually reproduce data magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

Operations as described herein can be carried out on or over a website. The website can be operated on a server computer, operated locally, e.g., by being downloaded to the client computer, or operated via a server farm. The website can be accessed over a mobile phone or a PDA, or on any other client. The website can use HTML code in any form, e.g., MHTML, or XML, and via any form such as cascading style sheets ("CSS") or other.

The computers described herein may be any kind of computer, either general purpose, or some specific purpose computer such as a workstation. The programs may be written in C, or Java, Brew, or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A hospital training method, comprising:
providing a central database associated with a processing server including a software system controlling operation of an inventory tracking and management system, the software system includes artificial intelligence and machine learning solutions;
registering storage devices comprising carts, cabinets, or shelves to the central database for inventory, wherein each of the storage devices including sensors, monitoring devices, and/or transmitting technology for transmitting information to the central database;
identifying, via the software system, inventory needs of the hospital;
storing preferences of doctors based upon information input into the system, wherein such information is accessed to optimize operations within the hospital;
generating lists of potential items needed in consideration of specific hospital employees on staff at a specific time; and
transmitting information to hospital employees based upon personal preferences of specific hospital staff as identified via artificial intelligence and machine learning solutions.

2. The hospital training method according to claim 1, wherein information generated by the sensors and/or monitoring devices is sent to the central database and the software system identifies aberrations that indicate incorrect inventory placement or low inventory levels.

3. The hospital training method according to claim 1, wherein transmitting information includes sending messages to hospital staff via computer devices.

4. The hospital training method according to claim 1, wherein transmitting information includes activating visual indicators associated with the carts, cabinets, or shelves.

5. The hospital training method according to claim 1, wherein transmitting information includes activating audio indicators associated with the carts, cabinets, or shelves.

6. The hospital training method according to claim 1, further including identifying a location of the storage devices and providing hospital staff with location information.

7. The hospital training method according to claim 1, further including identifying a location of inventory items and providing hospital staff with location information and/or information regarding misplaced inventory items.

8. The hospital training method according to claim 1, wherein identifying inventory needs of the hospital further includes sending alerts to hospital staff when items are out of stock.

9. A hospital training method, comprising:
providing a central database associated with a processing server including a software system controlling operation of an inventory tracking and management system, the software system includes artificial intelligence and machine learning solutions;
registering storage devices comprising carts, cabinets, or shelves to the central database for inventory, wherein each of the storage devices including sensors, monitoring devices, and/or transmitting technology for transmitting information to the central database;
identifying a location of the storage devices;
storing preferences of doctors based upon information, wherein such information is accessed to optimize operations within the hospital;
generating lists of potential items needed in in consideration of specific hospital employees on staff at a specific time; and
transmitting information to hospital employees based upon personal preferences of specific hospital staff as identified via artificial intelligence and machine learning solutions.

10. The hospital training method according to claim 9, wherein transmitting information includes sending messages to hospital staff via computer devices.

11. The hospital training method according to claim 9, wherein transmitting information includes activating visual indicators associated with the carts, cabinets, or shelves.

12. The hospital training method according to claim 11, wherein the visual indicators are lights.

13. The hospital training method according to claim 9, wherein transmitting information includes activating audio indicators associated with the carts, cabinets, or shelves.

14. The hospital training method according to claim 13, wherein the audio indicators are sound alarms.

15. The hospital training method according to claim 9, further including identifying a location of inventory items and providing hospital staff with location information and/or information regarding misplaced inventory items.

* * * * *